United States Patent [19]

Yamasaki

[11] Patent Number: 5,739,319

[45] Date of Patent: Apr. 14, 1998

[54] PHTHALOCYANINE OR NAPHTHALOCYANINE DERIVATIVE

[75] Inventor: Yasuhiro Yamasaki, Neyagawa, Japan

[73] Assignee: Orient Chemical Industries, Ltd., Osaka-fu, Japan

[21] Appl. No.: 713,610

[22] Filed: Sep. 13, 1996

[30] Foreign Application Priority Data

Sep. 14, 1995 [JP] Japan ................................. 7-236774

[51] Int. Cl.⁶ .................. C09B 67/12; C09B 47/24; C07D 487/22
[52] U.S. Cl. .................. 540/140; 540/122; 540/128; 540/136; 540/137; 430/270.17; 106/410; 106/411
[58] Field of Search ..................... 540/122, 128, 540/136, 137, 140; 430/270.17; 106/410, 411

[56] References Cited

U.S. PATENT DOCUMENTS

| | | | |
|---|---|---|---|
| 3,981,734 | 9/1976 | Cabut et al. | 106/288 |
| 4,622,179 | 11/1986 | Eda | 540/139 |
| 5,166,338 | 11/1992 | Büch et al. | 540/130 |
| 5,608,053 | 3/1997 | Thetford et al. | 540/140 |

*Primary Examiner*—Mukund J. Shah
*Assistant Examiner*—Pavanaram K. Sripada
*Attorney, Agent, or Firm*—Birch, Stewart, Kolasch & Birch, LLP

[57] ABSTRACT

A green or near infrared light absorbing water-soluble phthalocyanine or naphthalocyanine derivative which has excellent water resistance after dyeing, is provided. The present invention provides a phthalocyanine or naphthalocyanine derivative represented by the formula:

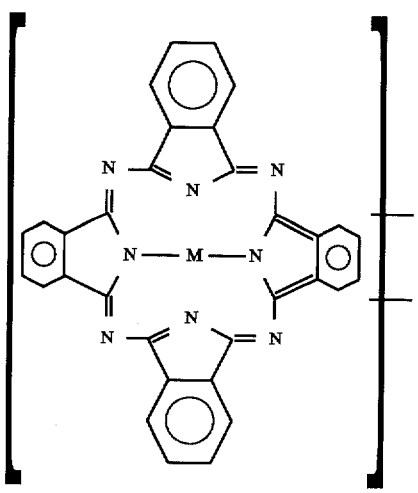

[I]

-continued

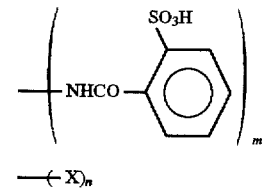

or

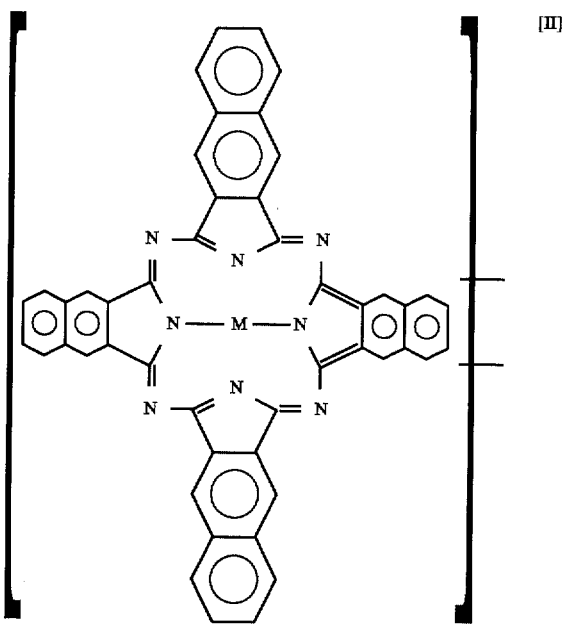

[II]

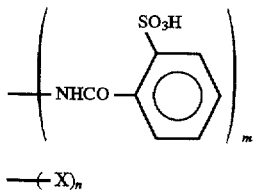

wherein X represents a halogen atom substituted at nucleus; M represents two hydrogen atoms, a divalent metal atom, a trivalent mono-substituted metal atom, or a tetravalent di-substituted metal atom; m represents 4 or 8; and n represents an integer of 0 to 12.

20 Claims, 4 Drawing Sheets

PHTHALOCYANINE OR NAPHTHALOCYANINE DERIVATIVE

FIELD OF THE INVENTION

The present invention relates to a phthalocyanine or naphthalocyanine derivative. More particularly, the present invention relates to a green or near infrared light absorbing water-soluble phthalocyanine or naphthalocyanine derivative which is useful for aqueous ink, color filter, or photorecording materials (e.g., optical disks such as compact disk, video disk recorder, and digital video disk).

BACKGROUND OF THE INVENTION

A phthalocyanine based organic pigment is excellent in fastness and permanence, and it is employed as blue colorant for paint or plastics. Furthermore, a chlorinated phthalocyanine pigment, and the like are also used as phthalocyanine green.

However, the phthalocyanine based pigment is insoluble in an organic solvent or water. Thus, it is required that the pigment is finely divided when it is used, according to the manner usually employed for making a pigment dispersion such as acid pasting. Moreover, a complicated finely dispersing treatment is required in order to use the pigment for aqueous pigment ink.

On the other hand, the phthalocyanine dyes which are classified into C.I. Solvent Blue-25 and -70 are known that they are soluble in an organic solvent. This type of oil-soluble dye is generally obtained by chlorosulfonating a (copper) phthalocyanine pigment, and allowing the resultant to react with aliphatic amine, or the like, to introduce sulfonamide groups into the phthalocyanine nucleus. As a water-soluble phthalocyanine dye, it is known the dye that has two to four sulfone groups or carboxyl groups on the phthalocyanine nucleus, or the dye that has sulfonamide groups substituted by hydroxyalkylamine on the phthalocyanine nucleus (Japanese Patent Kokoku Publication No. 24866/1990).

Recently, the water-soluble phthalocyanine dye is noticed as a colorant for aqueous ink, color filter, or photorecording materials, and it is used practically. However, most of them are in blue or cyan color, and green water-soluble phthalocyanine dye is scarcely known. Although C.I. Direct Blue-86, -87, C.I. Acid Blue-249, and the like which belong to copper phthalocyanine family, have been employed as a complementary-color colorant for green, but they are insufficient in water-solubility and water resistance after dyeing.

SUMMARY OF THE INVENTION

An object of the present invention is to provide a green or near infrared light absorbing water-soluble phthalocyanine or naphthalocyanine derivative which has excellent water resistance after dyeing.

The present invention provides a phthalocyanine or naphthalocyanine derivative represented by the formula:

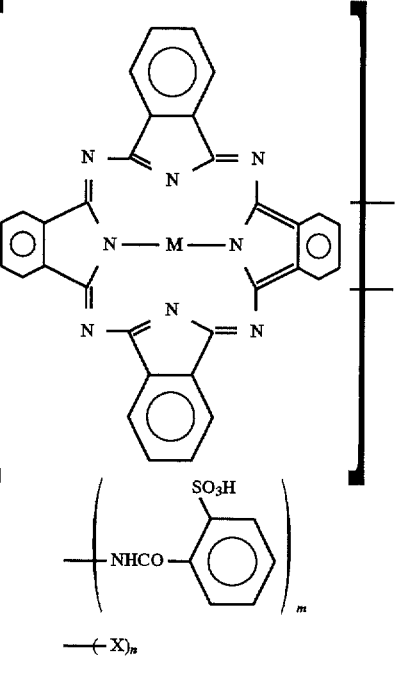

or

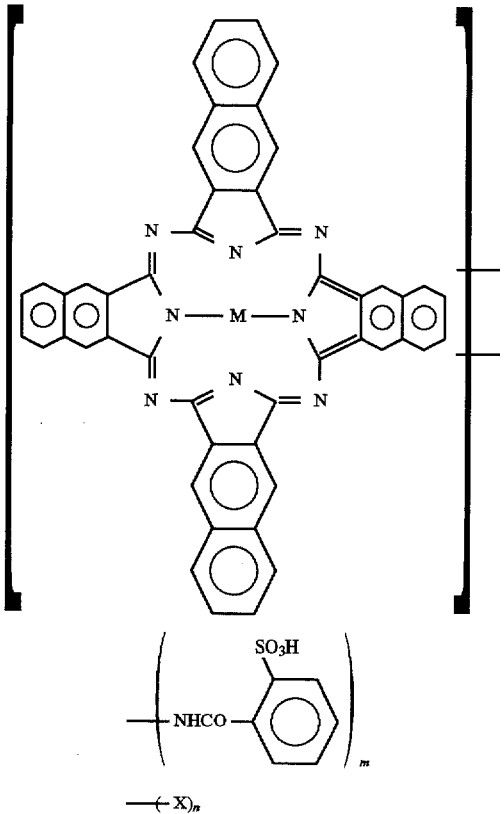

wherein X represents a halogen atom substituted at nucleus; M represents two hydrogen atoms, a divalent metal atom, a trivalent mono-substituted metal atom, or a tetravalent di-substituted metal atom; m represents 4 or 8; and n represents an integer of 0 to 12.

DETAILED DESCRIPTION OF THE INVENTION

Figure 1:
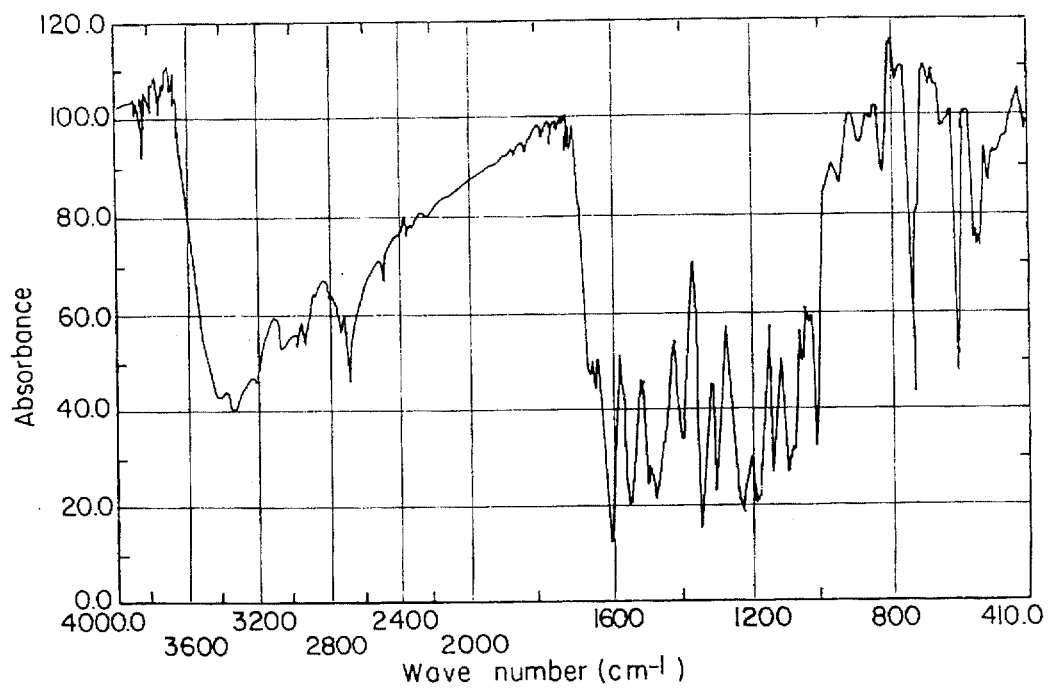
FIG. 1 is the IR spectrum of the phthalocyanine derivative prepared in Example 1.

In phthalocyanine or naphthalocyanine according to the present invention represented by formula [I] or [II], o-sulfobenzamide groups, and X are nucleus-substituents which are present on the phthalocyanine or naphthalocyanine nucleus. X represents a halogen atom such as Cl, Br, I, and F, and preferably Cl or Br.

Phthalocyanine or naphthalocyanine according to the present invention contains 4 or 8 o-sulfobenzamide groups as the substituents. That is, four benzene rings or four naphthalene rings which constitute the phthalocyanine nucleus or the naphthalocyanine nucleus, contains either one o-sulfobenzamide group or two o-sulfobenzamide groups, respectively. The preferred number of o-sulfobenzamide group is 4.

Phthalocyanine or naphthalocyanine according to the present invention contains 0 to 12 halogen atoms as peripheral substituents. The number of the halogen atoms may suitably be adjusted depending on the desired color tone. The preferred number of the halogen atoms is 0 to 4.

M represents two hydrogen atoms (2H), a divalent metal atom, a trivalent mono-substituted metal atom, or a tetravalent di-substituted metal atom.

The term "two hydrogen atoms" used herein means two hydrogen atoms which independently bond to nitrogen atoms. Accordingly, in this case, M represents two independent hydrogen atoms which respectively form two imino groups (=N—H) with the nitrogen atoms facing each other at the central portion of the formula. When M is two hydrogen atoms, formula [I] or [II] represents non-metallo phthalocyanine or naphthalocyanine.

Examples of the divalent metal atom include Cu, Zn, Fe, Co, Ni, Pb, Pt, Pd, Mn, Sn, Mg, Ba, Ca, Ti, Be, and the like. Preferred are Cu, Ni, Co, and Fe.

The term "trivalent mono-substituted metal atom" used herein means the trivalent metal atom of which one valence is served for bonding with a substituent, and the other two valences are served for bonding with the nitrogen atoms in the above described formula. Examples of the trivalent metal atom include Al, Ga, In, Ti, Mn, Fe, and the like, and preferred are Al, Ga, and the like. Examples of the substituent include halogen atoms such as Cl, F, Br, and I; alkoxy groups such as a methoxy group, an ethoxy group, and a propoxy group; a phenoxy group; a hydroxy group, and the like. Examples of the "trivalent mono-substituted metal atom" include AlCl, GeCl, InCl, Al(O-alkyl), Al(O-phenyl), Ga(O-alkyl), Ga(O-phenyl), Al(OH), and Ga(OH).

The term "tetravalent di-substituted metal atom" used herein means the tetravalent metal atom of which two valences are served for bonding with substituents, and the other two valences are served foe bonding with nitrogen atoms in the above described formula. Examples of the tetravalent metallic atom include Cr, Si, Ge, V, Fin, Ti, and the like, preferred are Ge, Si, V, Ti, and the like; and more preferred are Ti, and V. Examples of the substituent include an oxygen atom, and those described above for the trivalent metal atom, and the like. Examples of the "tetravalent di-substituted metal atom" include $GeCl_2$, $SiF_2$, $TiCl_2$, $Si(O-alkyl)_2$, $Ge(O-alkyl)_2$, $Si(O-phenyl)_2$, $Ge(O-phenyl)_2$, $Ge(OH)_2$, and the like. When the substituent is an oxygen atom, the examples include V=O, Mn=O, Ti=O, and the like.

It is preferred that the phthalocyanine derivative according to the present invention is prepared according to the process which comprises the step of: reacting amino metallo or non-metallo phthalocyanine with o-sulfobenzoic acid anhydride in the presence of a reaction accelerator in an aprotic organic solvent.

The term "amino metallo or non-metallo phthalocyanine" means the metallo or non-metallo phthalocyanine derivative which has amino groups on the phthalocyanine nucleus. In the present invention, tetraamino metallo or non-metallo phthalocyanine which has four amino groups, or octaamino metallo or non-metallo phthalocyanine which has eight amino groups is employed. These amino metallo or non-metallo phthalocyanines may further contain the other substituents which do not react with the amino groups under a usual reaction condition.

The other substituents preferred are halogen atoms. This is why a color tone of the resulting phthalocyanine derivative can be controlled dependent upon the kind, and the number of the halogen atoms which is present on the phthalocyanine nucleus.

Amino metallo or non-metallo phthalocyanine can be synthesized by a method well known to those skilled in the art.

For example, tetranitro metallo (Cu) or non-metallo phthalocyanine is obtained from 4-nitrophthalonitrile according to the phthalonitrile method, and then it is reduced to obtain tetraamino metallo (Cu) or non-metallo phthalocyanine. Furthermore, 4,5-dinitrophthalonitrile can be used as a raw material to prepare octaamino metallo or non-metallo phthalocyanine. Otherwise, 4-nitro-5-chlorophthalonitrile can be used as a raw material to prepare tetrachlorotetraamino metallo or non-metallo phthalocyanine.

"Shikizai (Coloring Material)"; Shikizai Kyohkai-shi (Journal of Association of Coloring Material), 38, 100–109, 1964, discloses the method which comprises the steps of: preparing tetranitro metallo (Cu) phthalocyanine by using 4-nitro-phthalimide or 4-nitrophthalic acid arthydride as a raw material (Wyler method); and then reducing it to obtain tetraamino metallo (Cu) phthalocyanine. It also discloses another method which comprises the steps of: preparing tetrachlorotetranitro metallo (Cu) phthalocyanine by using 4-chloro-5-nitrophthalimide as a raw material (Wyler method); and then reducing it to obtain tetrachlorotetraamino metallo (Cu) phthalocyanine.

These methods are shown in the following schema:

(i) Phthalonitrile method (ii) Wyler method (Urea method)

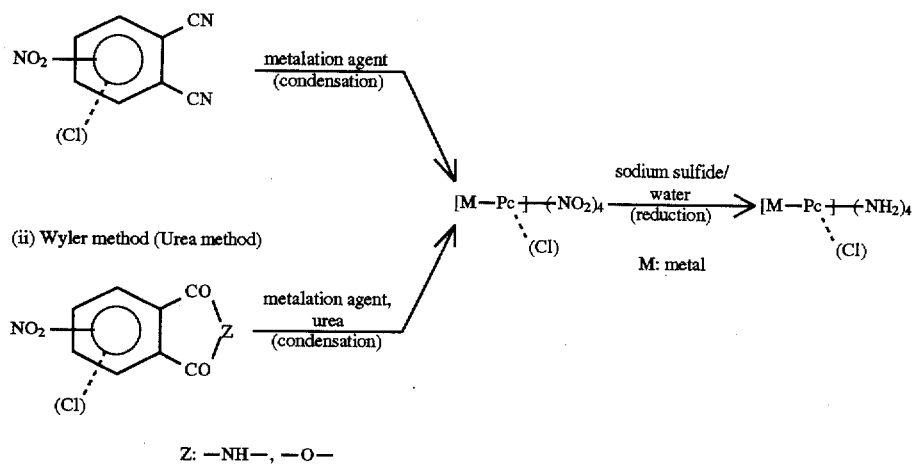

Z: —NH—, —O—

Examples of amino metallo or non-metallo phthalocyanine preferred to be used in the present invention include tetraamino metallo or non-metallo phthalocyanines, tetrachlorotetraamino metallo or non-metallo phthalocyanines, octaamino metallo or non-metallo phthalocyanines, tetrabromotetraamino metallo or non-metallo phthalocyanines, and polychlorotetraamino metallo or non-metallo phthalocyanines.

Thereafter, amino metallo or non-metallo phthalocyanine thus obtained is allowed to react with o-sulfobenzoic acid anhydride in the presence of a reaction accelerator in an aprotic organic solvent. An amino group of amino metallo or non-metallo phthalocyanine reacts with an acid anhydride group of o-sulfobenzoic acid anhydride, and an amide bond is formed. As a result, an o-sulfonamide group is introduced into the phthalocyanine nucleus to produce the phthalocyanine derivative represented by the formula [I] of the present invention.

It is preferred that amino metallo or non-metallo phthalocyanine, and o-sulfobenzoic acid anhydride are reacted in approximately the equivalent ratio. Since amino metallo or non-metallo phthalocyanine used in the present invention has four or eight amino groups, 4 or 8 mol of o-sulfobenzoic acid anhydride is usually employed with respect to 1 mol of amino metallo or non-metallo phthalocyanine. Preferably, 1 to 1.5 equivalent of o-sulfobenzoic acid anhydride is used with respect to 1 amino group of amino metallo or non-metallo phthalocyanine.

As the aprotic organic solvent, pyridine, N,N-dimethylformamide, N,N-dimethylacetamide, N-methyl-2-pyrrolidone, and the like may be employed. Pyridine is preferable. An amount of the solvent to be used is not particularly limited, but it is usually 5 to 50 times in weight, and preferably 10 to 30 times in weight based on the weight of amino metallo or non-metallo phthalocyanine.

As the reaction accelerator (basic catalyst), triethylamine, tributylamine, N-metylpiperidine, triethylenediamine, 4-dimetylaminopyridine, and the like may be employed. Preferred is triethylamine. An amount of the reaction accelerator to be used is usually 2 to 5 times equivalent, preferably 3 to 4 times equivalent with respect to 1 amino group of amino metallo or non-metallo phthalocyanine.

The reaction is conducted in the manner that each predetermined amounts of amino metallo or non-metallo phthalocyanine, o-sulfobenzoic acid anhydride, and the reaction accelerator are dissolved in the aprotic organic solvent, and the solution is stirred at a temperature of 50° C. or more, preferably under reflux of the solvent used for 0.5 to 5 hours, preferably 1 to 2 hours.

The resulting phthalocyanine derivative according to the present invention may optionally be further halogenated. Halogenation is carried out by a method well known to those skilled in the art.

The naphthalocyanine derivative according to the present invention is obtained by the same procedure as that described above except that amino metallo or non-metallo naphthalocyanine is employed instead of amino metallo or non-metallo phthalocyanine. A synthesis of the amino metallo or non-metallo naphthalocyanine may also be conducted according to the same procedure as that of amino metallo or non-metallo phthalocyanine, except that nitronaphthalonitrile or nitronaphthalimide is employed as a raw material.

Preferably, the naphthalocyanine derivative according to the present invention is obtained by the method which comprises the step of: reacting amino metallo or non-metallo naphthalocyanine selected from the group consisting of tetraamino metallo or non-metallo naphthalocyanines, and octaamino metallo or non-metallo naphthalocyanines, with o-sulfobenzoic acid anhydride in the presence of the reaction accelerator in the aprotic organic solvent.

The phthatocyanine or naphthalocyanine derivative of the present invention is useful for a colorant for aqueous ink, and it provides a high-quality printed image (i.e., the clear image having water resistance, high optical density, and no bleeding) when it is used for ink-jet printing ink.

The phthalocyanine or naphthalocyanine derivative provides an optical element having good transparency when it is used for a colorant for color filter. Particularly, the naphthalocyanine derivative is useful for near infrared light absorbing color filter.

Furthermore, the phthalocyanine and naphthalocyanine derivative of the present invention are useful for a colorant for photorecording materials.

EXAMPLES

The present invention is illustrated by the following Examples which, however, are not to be construed as limiting the present invention to their details.

Synthesis Example 1

Synthesis of tetraamino copper phthalocyanine

To 400 g of sulfolane were added 64.0 g of 4-nitrophthalimide, 84.4 g of urea, 10.0 g of cuprous chloride, and 1.0 g of ammonium molybdate, the admixture was heated to 180° C., and stirred at a temperature of 180° to 190° C. for 6 hours to react them. The reaction mixture was cooled to 140° C., and was filtered while the reaction mixture was maintained at a temperature of 120° to 140° C. The separated solid was washed with methanol, and was further rinsed with water. Thereafter, the solid was heat-treated with 0.1% dilute aqueous sodium hydroxide, further heat-treated with dilute aqueous hydrochloric acid, and was filtrated, rinsed with water, and dried. The product was dissolved in 98% concentrated sulfuric acid, the solution was poured into water, and the resulting precipitate was filtrated, rinsed with water, and dried. Furthermore, the product was boil-treated in N,N'-dimethylformamide, filtrated, and thereafter was rinsed with hot water to obtain a wet cake of purified tetra(4)nitro copper phthalocyanine.

The wet cake of finely divided purified tetra(4)nitro copper phthalocyanine was suspended into 1000 ml of water, to which were added 200 g of sodium sulfate (9 hydrates) at room temperature. The admixture was stirred at 30° C. for 3 hours, and further at 60° C. for four hours to reduce the tetra(4)nitro copper phthalocyanine. The product was filtrated, rinsed with water, dried, and further the product thus treated was heat-treated with dioxane, thereafter dissolved in 98% concentrated sulfuric acid. The resulting solution was then added to a large amount of water. The precipitate was filtrated, rinsed with water, and neutralized with a dilute aqueous sodium hydroxide to liberate tetraamino copper phthalocyanine. The resulting product was rinsed with water, and dried to obtain 43.0 g of purified tetra(4)amino copper phthalocyanine.

Synthesis Example 2

Synthesis of tetraamino non-metallo phthalocyanine 25.0 g of 4-nitrophthalonitrile, and 200 g of amyl alcohol had been previously heated, and stirred at 80° to 90° C., to which was dropped 10 g of DBU over 15 minutes, and then it was heated and stirred at 140° to 143° C., and refluxed for 3 hours. After thermal filtration, substantially the same procedures as those of Synthesis Example 1 were conducted. That is, finely divided tetranitro non-metallo phthalocyanine was suspended into 300 ml of water, and reduced by using 70 g of sodium sulfate 9 hydrates to obtain 10.6 g of tetraamino non-metallo phthalocyanine.

Synthesis Example 3

Synthesis of tetrachlorotetraamino copper phthalocyanine

To 100 g of sulfolane was added 18.7 g of 4-chloro-5-nitrophthalimide, 21.1 g of urea, and 2.2 g of cuprous chloride, the admixture was heated, and allowed to react at a temperature of 180° to 190° C. for 5.5 hours. The reaction mixture was cooled to 140° C., then was thermally filtrated. The resulting solid was washed with methanol, and further rinsed with water. Thereafter, purified tetrachlorotetranitro copper phthalocyanine was obtained according to the same procedures as that of Synthesis Example 1. Then, the resulting purified tetrachlorotetranitro copper phthalocyanine was reduced to obtain 13.4 g of purified tetrachlorotetraamino copper phthalocyanine.

Example 1

Synthesis of tetrakis(sulfobenzamide) copper phthalocyanine ($C_{60}H_{36}N_{12}O_{16}S_4Cu=1371.5$)

A mixture of 12.7 g (20 mmol) of tetraamino copper phthalocyanine obtained in Synthesis Example 1, 300 ml of pyridine, and 30 ml of triethylamine was previously stirred at 80° C. for 30 minutes. To the mixture thus stirred were gradually added 18.4 g of o-sulfobenzoic acid anhydride over 15 minutes. After the addition, the reaction mixture was stirred and refluxed for 1 hour. After allowing the mixture to cool to 80° C., insoluble matters were removed by passing the mixture through a glass filter. A solvent was distilled away from the resulting solution by the use of an evaporator. To the resulting solid were added 200 ml of acetone, and stirred and refluxed for 1 hour to prepare a slurry. After filtration, 200 ml of acetone was sprinkled over the resulting product for washing, thereafter it was vacuum dried to obtain 15.03 g (54.3% yield) of green solid.

Figure 2:
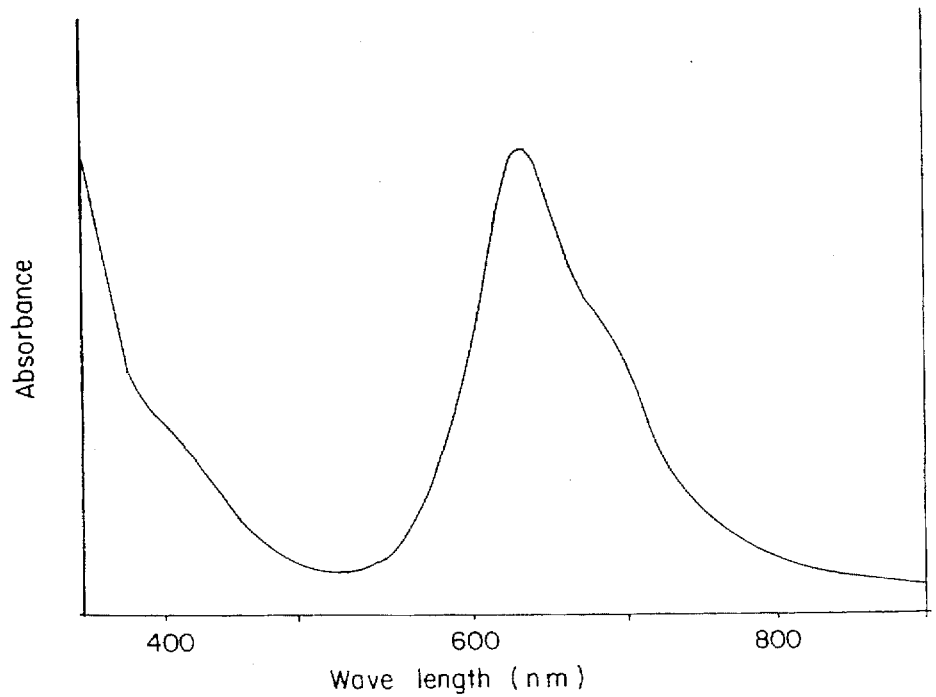
FIG. 2 is the visible light absorbing spectrum of the phthalocyanine derivative prepared in Example 1.

The resulting compound was identified by the following analyses. IR and visible light absorption spectra of the compound are shown in FIGS. 1 and 2, respectively.

TABLE 1

| | Elemental Analysis | | | |
|---|---|---|---|---|
| | C | H | N | Cu |
| Calculated | 52.50 | 2.62 | 12.25 | 4.63 |
| Found | 52.70 | 2.70 | 12.29 | 4.01 |

IR absorption (KBr,cm$^{-1}$)

$\upsilon$=3340,3054,2679,1668,1606,1558,1506,1489,1436, 1405, 1348,1299,1228,1189,1140,1097,1018,746,617

Visible light absorption (aqueous solution)

$\lambda max$=638.2 nm $\epsilon$=3.76×10$^4$

Then, solubility at room temperature of the resulting compound is measured. The following Table 2 shows the results.

TABLE 2

| Solubility | |
|---|---|
| Water | >10% |
| Methanol | >5% |
| Acetone | insoluble |

Example 2

Synthesis of tetrakis(sulfobenzamide) phthalocyanine ($C_{60}H_{36}N_{12}O_{16}S_4$=1310)

1.18 g (52.2% yield) of green solid was obtained according to substantially the same procedure as described in Example 1, except that 1.0 g of tetraamino non-metallo phthalocyanine prepared in Synthesis Example 2, 30 ml of pyridine, 3 ml of triethylamine, and 1.5 g of o-sulfobenzoic acid anhydride were used.

Figure 3:
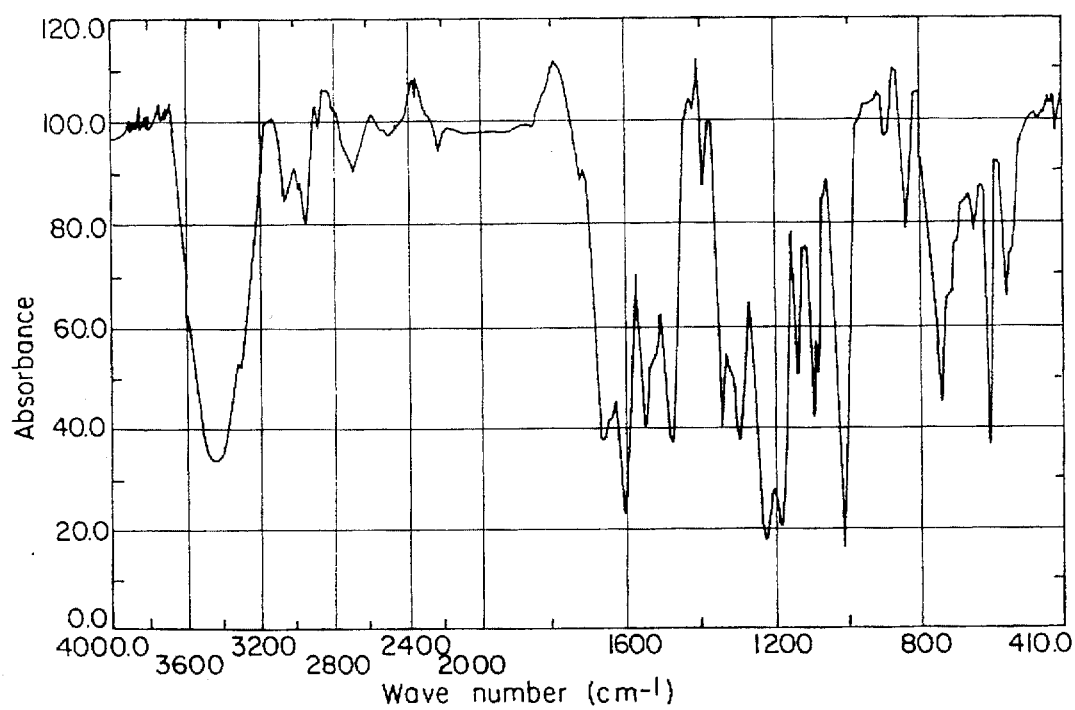
FIG. 3 is the IR spectrum of the phthalocyanine derivative prepared in Example 2.
Figure 4:
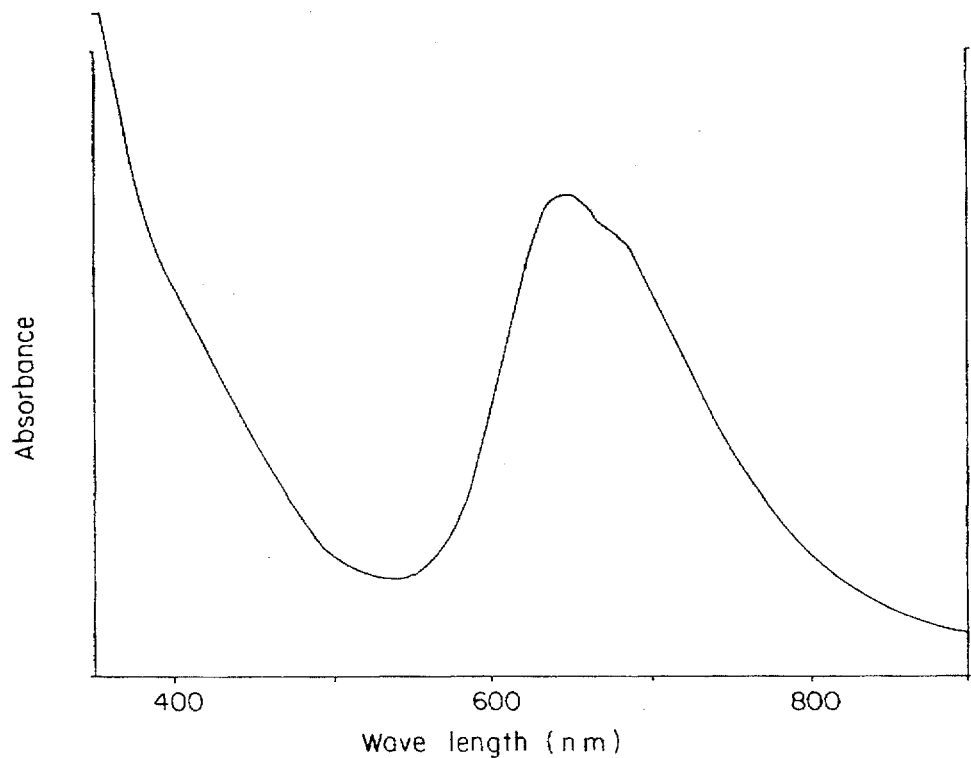
FIG. 4 is the visible light absorbing spectrum of the phthalocyanine derivative prepared in Example 2.

The resulting compound was identified by the following analyses. IR and visible light absorption spectra of the compound are shown in FIGS. 3 and 4, respectively.

TABLE 3

| | Elemental Analysis | | |
|---|---|---|---|
| | C | H | N |
| Calculated | 54.96 | 2.90 | 12.82 |
| Found | 55.39 | 3.04 | 12.92 |

IR absorption (KBr,cm$^{-1}$)

$\upsilon$=3450,3296,3060,2680,1666,1606,1554,1482,1346, 1299, 1230,1192,1140,1097,1020,752,617

Visible light absorption (aqueous solution)

$\lambda$max=650.0 nm $\epsilon$=2.56×10$^4$

Then, solubility at room temperature of the resulting compound is measured. The following Table 4 shows the results.

TABLE 4

| Solubility | |
|---|---|
| Water | >10% |
| Methanol | >5% |
| Acetone | insoluble |

Example 3

Synthesis of tetrachlorotetrakis(sulfobenzamide) copper phthalocyanine (C$_{60}$H$_{36}$N$_{12}$O$_{16}$Cl$_4$S$_4$Cu= 1509.5)

16.4 g of green solid was obtained according to substantially the same procedure as described in Example 1, except that 14.1 g (20 mmol) of tetrachlorotetraamino copper phthalocyanine, 300 ml of pyridine, 30 ml of triethylamine, and 18.4 g of o-sulfobenzoic acid anhydride were used.

The resulting compound was identified according to the same manner as described in Example 1.

Example 4

Synthesis of tetrakis(sulfobenzamide) nickel naphthalocyanine (C$_{76}$H$_{44}$N$_{12}$O$_{16}$S$_4$Ni=1566.7)

5-Nitro-1,2-dicyanonaphthalene was synthesized according to the conventional method, and it was condensed with nickel chloride in quinoline to obtain tetranitro nickel naphthalocyanine. Nitro groups of the tetranitro nickel naphthalocyanine were reduced according to the same manner as described in Synthesis Example 1, to obtain tetraamino nickel naphthalocyanine.

0.433 g (76.8% yield) of yellow-green solid was obtained according to substantially the same procedure as described in Example 1, except that 0.30 g of the resulting tetraamino nickel naphthalocyanine, 3 ml of pyridine, 0.33 ml of triethylamine, and 0.67 g of o-sulfobenzoic acid anhydride were used.

Figure 5:
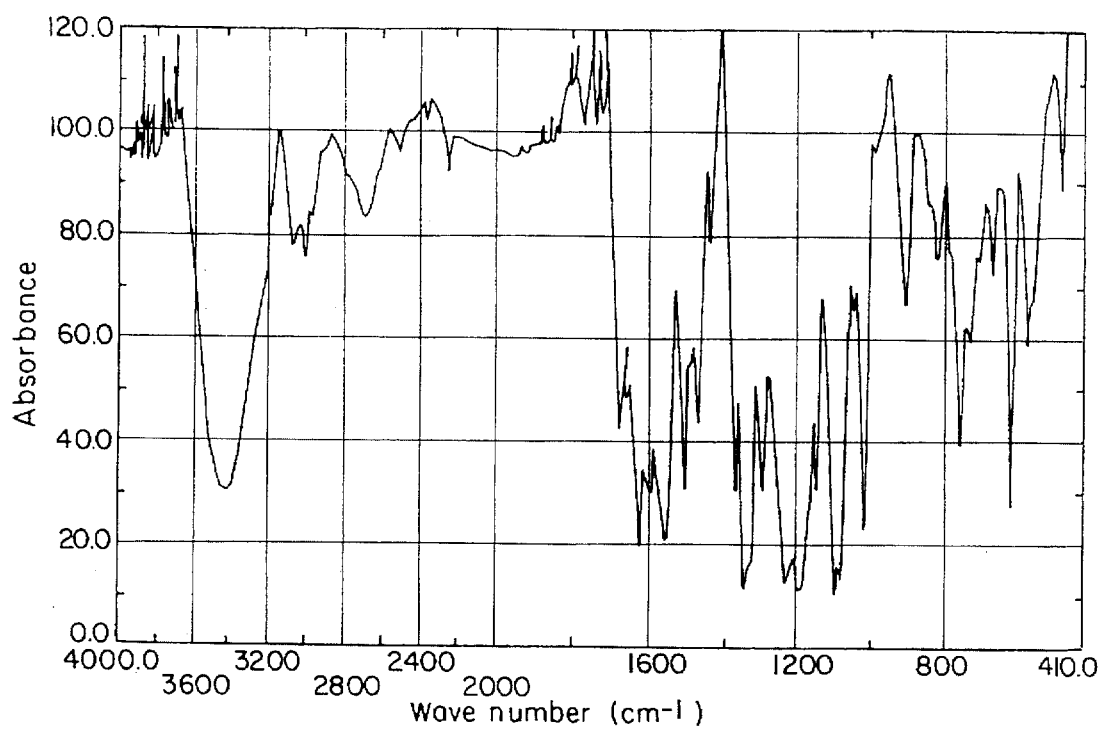
FIG. 5 is the IR spectrum of the naphthalocyanine derivative prepared in Example 4.
Figure 6:
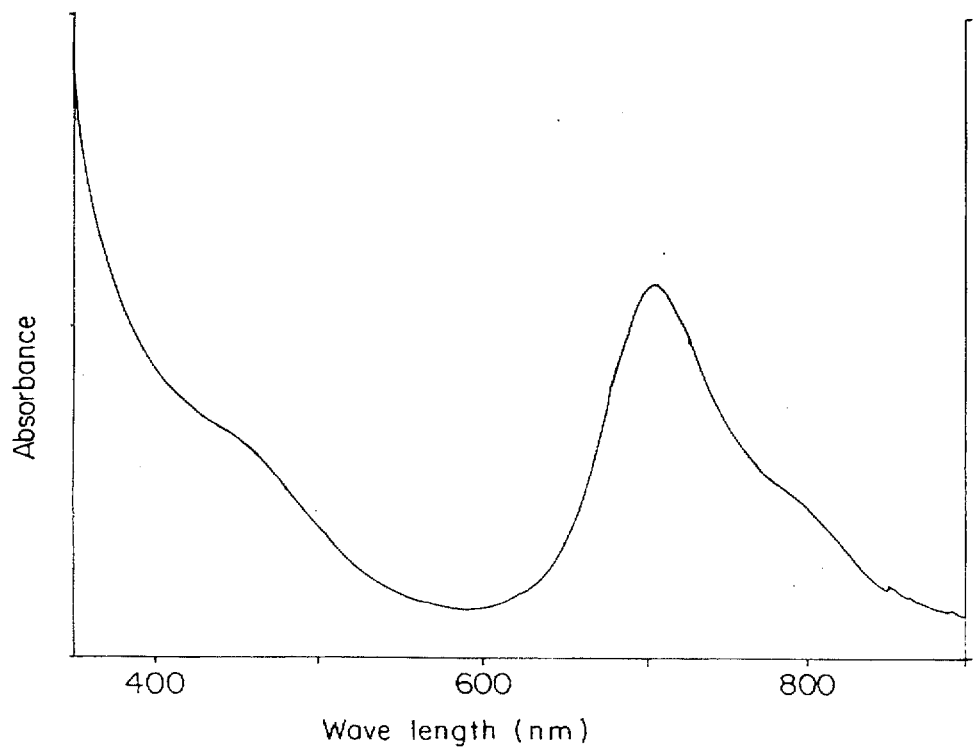
FIG. 6 is the visible light absorbing spectrum of the naphthalocyanine derivative prepared in Example 4.

The resulting compound was identified by the following analyses. IR and visible light absorption spectra of the compound are shown in FIGS. 5 and 6, respectively.

TABLE 5

| | Elemental Analysis | | | |
|---|---|---|---|---|
| | C | H | N | Ni |
| Calculated | 58.21 | 2.81 | 10.72 | 3.75 |
| Found | 58.61 | 2.74 | 10.37 | 3.67 |

IR absorption (KBr,cm$^{-1}$)

$\upsilon$=3437,3052,2680,1664,1620,1595,1554,1502,1461, 1371, 1342,1290,1228,1190,1140,1097,1082,1018,752,617

Visible light absorption (aqueous solution)

$\lambda$max=708.2 nm $\epsilon$=2.35×10$^4$

Then, solubility at room temperature of the resulting compound is measured. The following Table 6 shows the results.

TABLE 6

| Solubility | |
|---|---|
| Dilute aqueous alkaline solution | <1.5% |
| Methanol | <0.1% |
| DMF | >2.0% |
| Acetone | insoluble |

Example 5

Synthesis of tetrakis(sulfobenzamide) copper naphthalocyanine (C$_{76}$H$_{44}$N$_{12}$O$_{16}$S$_4$Cu=1571.5)

5-Nitro-1,2-dicyanonaphthalene was synthesized according to the conventional method, and it was condensed with copper chloride in quinoline to obtain tetranitro copper naphthalocyanine. Nitro groups of the tetranitro nickel naphthalocyanine were reduced according to the same manner as described in Synthesis Example 1, to obtain tetraamino copper naphthalocyanine.

0.266 g (47.0% yield) of yellow-green solid was obtained according to substantially the same procedure as described in Example 1, except that 0.30 g of the resulting tetraamino copper naphthalocyanine, 3 ml of pyridine, 0.33 ml of triethylamine, and 0.67 g of o-sulfobenzoic acid anhydride were used.

Figure 7:
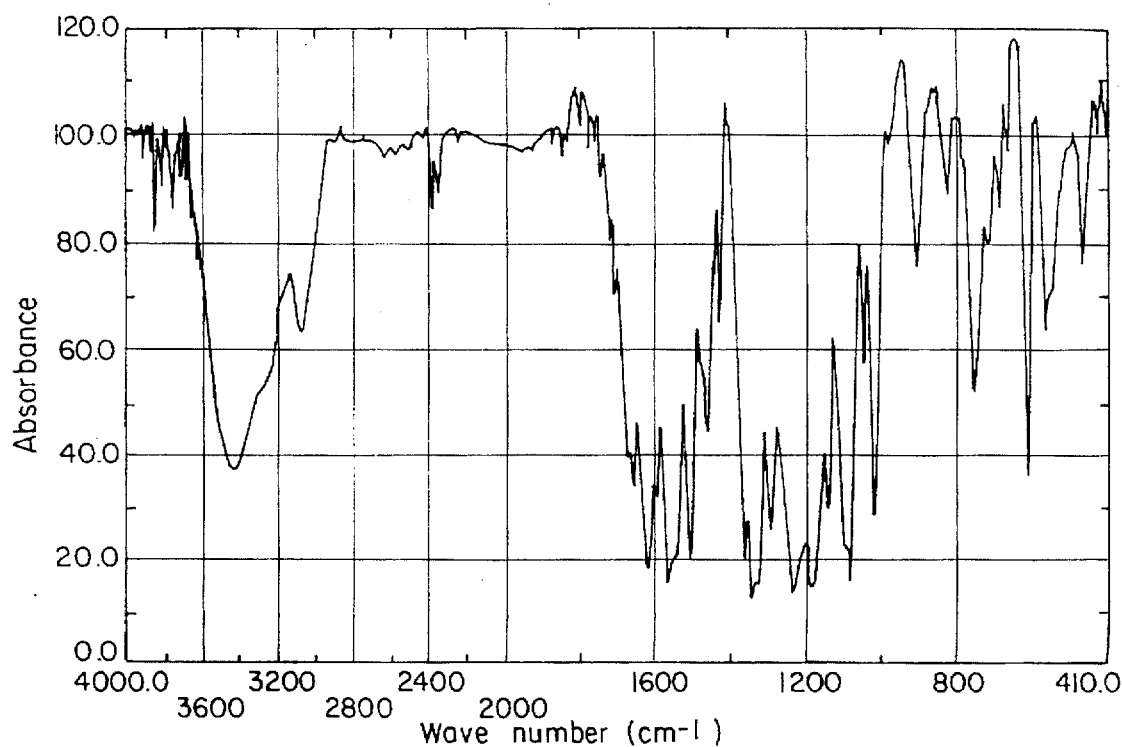
FIG. 7 is the IR spectrum of the naphthalocyanine derivative prepared in Example 5.
Figure 8:
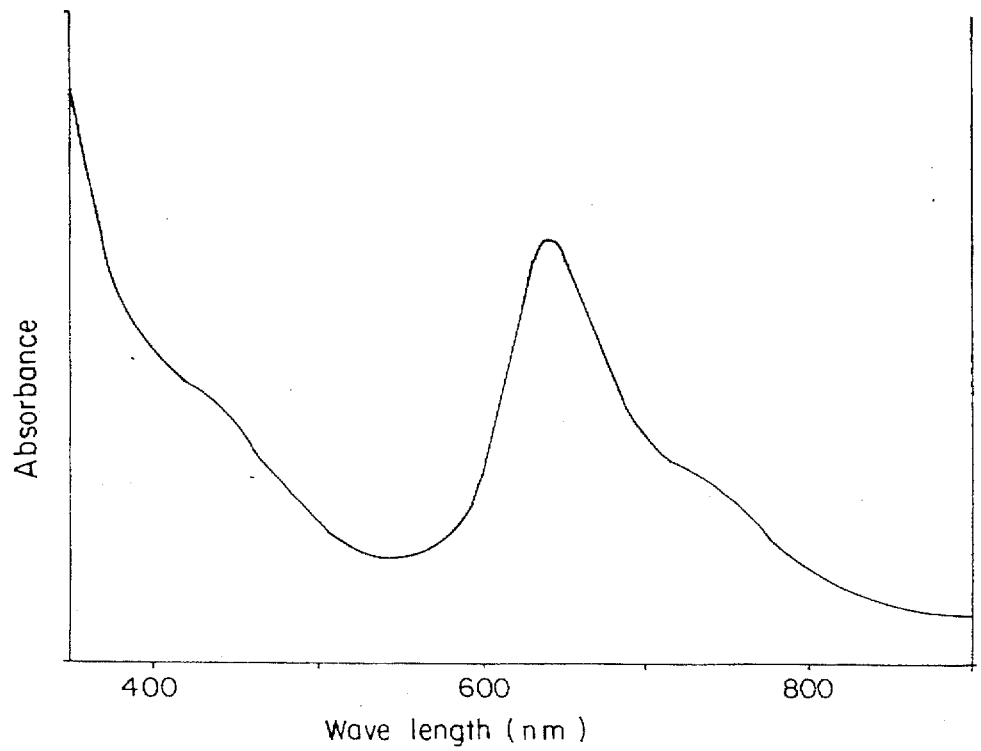
FIG. 8 is the visible light absorbing spectrum of the naphthalocyanine derivative prepared in Example 5.

The resulting compound was identified by the following analyses. IR and visible light absorption spectra of the compound are shown in FIGS. 7 and 8, respectively.

TABLE 7

| | Elemental Analysis | | | |
|---|---|---|---|---|
| | C | H | N | Cu |
| Calculated | 58.03 | 2.80 | 10.69 | 4.04 |
| Found | 58.33 | 2.91 | 10.32 | 4.01 |

IR absorption (KBr,cm$^{-1}$)

$\upsilon$=3427,3062,1668,1616,1595,1558,1540,1500,1458, 1363, 1342,1327,1290,1230,1186,1140,1082,1018,746,615

Visible light absorption (aqueous solution)

$\lambda$max=696.4 nm

ε=3.10×10⁴

Then, solubility at room temperature of the resulting compound is measured. The following Table 8 shows the results.

TABLE 8

| Solubility | |
| --- | --- |
| Dilute aqueous alkaline solution | <1.5% |
| Methanol | <0.1% |
| DMF | >2.0% |
| Acetone | insoluble |

Applied Example (Aqueous ink for ink-jet printing)

Aqueous ink 1 for ink-jet printing of the present invention having pH of 7.7, was prepared by using the combination represented in Table 9. Tetrakis(sulfobenzamide) copper phthalocyanine of Table 9 was prepared in Example 1.

TABLE 9

| Ion exchanged water | 88.2% |
| --- | --- |
| N-methyl-2-pyrrolidone | 4.9% |
| Ethanol | 4.9% |
| Tetrakis(sulfobenzamide) copper phthalocyanine | 2.0% |

Aqueous ink 2 for ink-jet printing for comparison having pH of 6.9, was prepared by using the combination represented in Table 10. Tetrasulfonic acid copper phthalocyanine (C.I. acid blue 249) of Table 10 was prepared according to Wyler method from 4-sodium sulfophthalic acid anhydride.

TABLE 10

| Ion exchanged water | 88.2% |
| --- | --- |
| N-methyl-2-pyrrolidone | 4.9% |
| Ethanol | 4.9% |
| Tetrasulfonic acid copper phthalocyanine | 2.0% |

Thus prepared ink 1 and ink 2 were printed on a high-grade copying paper by using the ink-jet printer manufactured by Seiko Epson K.K. "HG5130". Water resistance of the printed ink 1 and ink 2 which were printed on the paper, was evaluated according to the following procedure.

The papers printed by using ink 1 and ink 2 were dried in air for 24 hours or more. The papers were then dipped in flow water for 30 seconds, and dried in air. Optical density of ink on the dried papers was respectively measured by using the densitometer "MACBETH TR927". The ratio in percentage of the optical density after dipping based on those of before dipping is calculated. The results are shown in Table 11.

TABLE 11

| Filter | Ink 1 | Ink 2 |
| --- | --- | --- |
| WHITE | 71% | 53% |
| RED | 67% | 59% |
| GREEN | 68% | 46% |
| BLUE | 68% | 45% |

Water resistance of ink 1 and ink 2 which were printed on the paper, was further evaluated according to substantially the same manner as described above, except that the printed papers were dipped in static water for 1 hour. The results are shown in Table 12.

TABLE 12

| Filter | Ink 1 | Ink 2 |
| --- | --- | --- |
| WHITE | 73% | 16% |
| RED | 70% | 15% |
| GREEN | 70% | 17% |
| BLUE | 70% | 22% |

The results of the evaluation described above show that the ink which was prepared by using a phthalocyanine derivative of the present invention has excellent water resistance by comparison with those which was prepared by using a conventional water soluble phthalocyanine derivative.

What is claimed is:

1. A phthalocyanine derivative represented by the formula:

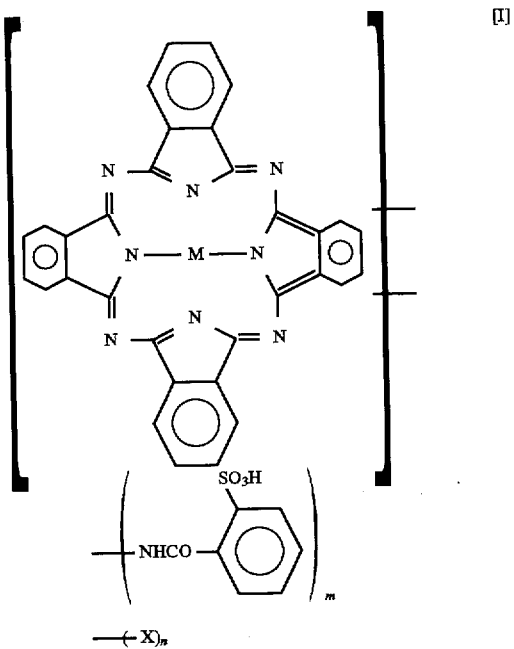

wherein X represents a halogen atom substituted at nucleus; M represents two hydrogen atoms, a divalent metal atom, a trivalent mono-substituted metal atom, or a tetravalent di-substituted metal atom; m represents 4 or 8; and n represents an integer of 0 to 12.

2. The phthalocyanine derivative according to claim 1, wherein the divalent metal atom is selected from the group consisting of Cu, Zn, Fe, Co, Ni, Pb, Pt, Pd, Mn, Sn, Mg, Ba, Ca, Ti, and Be.

3. The phthalocyanine derivative according to claim 1, wherein the trivalent mono-substituted metal atom is selected from the group consisting of AlCl, GeCl, InCl, Al(O-alkyl), Al(O-phenyl), Ga(O-alkyl), Ga(O-phenyl), Al(OH), and Ga(OH).

4. The phthalocyanine derivative according to claim 1, wherein the tetravalent di-substituted metal atom is selected from the group consisting of $GeCl_2$, $SiF_2$, $TiCl_2$, $Si(O-alkyl)_2$, $Ge(O-alkyl)_2$, $Si(O-phenyl)_2$, $Ge(O-phenyl)_2$, $Ge(OH)_2$, V=O, Mn=O, and Ti=O.

5. The phthalocyanine derivative according to claim 1, wherein m of formula [I] represents 4.

6. The phthalocyanine derivative according to claim 1, wherein n of formula [I] represents an integer of 0 to 4.

7. A process for producing phthalocyanine derivative which comprises the step of: reacting amino metallo or non-metallo phthalocyanine selected from the group consisting of tetraamino metallo or non-metallo phthalocyanines, and octaamino metallo or non-metallo phthalocyanines, with o-sulfobenzoic acid anhydride in the presence of a reaction accelerator in an aprotic organic solvent.

8. Aqueous ink for ink-jet printing which comprises water, and the phthalocyanine derivative according to claim 1 as a colorant.

9. Color filter which comprises the phthalocyanine derivative according to claim 1 as a colorant.

10. Photorecording materials which comprise the phthalocyanine derivative according to claim 1 as a colorant.

11. A naphthalocyanine derivative represented by the formula:

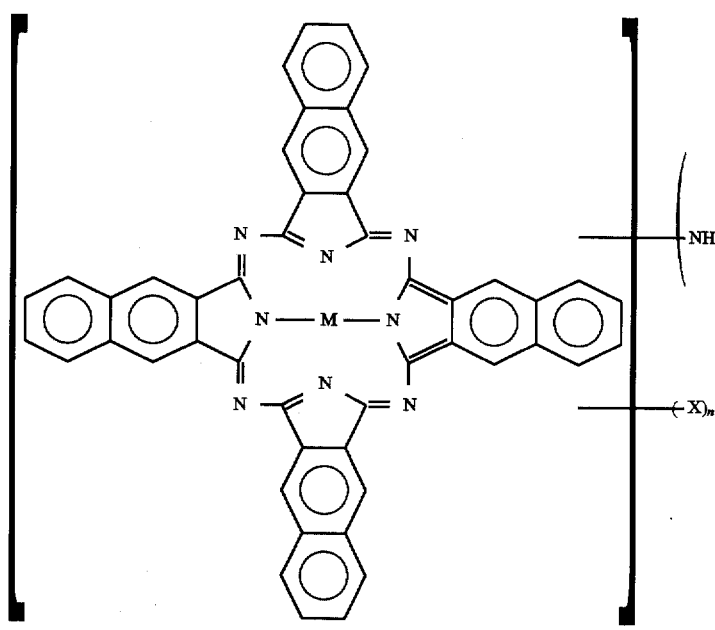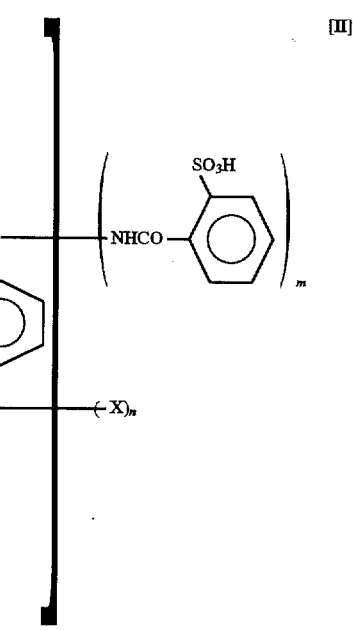

[II]

wherein X represents a halogen atom substituted at nucleus; M represents two hydrogen atoms, a divalent metal atom, a trivalent mono-substituted metal atom, or a tetravalent di-substituted metal atom; m represents 4 or 8; and n represents an integer of 0 to 12.

12. The naphthalocyanine derivative according to claim 11, wherein the divalent metal atom is selected from the group consisting of Cu, Zn, Fe, Co, Ni, Pb, Pt, Pd, Mn, Sn, Mg, Ba, Ca, Ti, and Be.

13. The naphthalocyanine derivative according to claim 11, wherein the trivalent mono-substituted metal atom is selected from the group consisting of AlCl, GeCl, InCl, Al(O-alkyl), Al(O-phenyl), Ga(O-alkyl), Ga(O-phenyl), Al(OH), and Ga(OH).

14. The naphthalocyanine derivative according to claim 11, wherein the tetravalent di-substituted metal atom is selected from the group consisting of $GeCl_2$, $SiF_2$, $TiCl_2$, $Si(O\text{-alkyl})_2$, $Ge(O\text{-alkyl})_2$, $Si(O\text{-phenyl})_2$, $Ge(O\text{-phenyl})_2$, $Ge(OH)_2$, V=O, Mn=O, and Ti=O.

15. The naphthalocyanine derivative according to claim 11, wherein m of formula [II] represents 4.

16. The naphthalocyanine derivative according to claim 11, wherein n of formula [II] represents an integer of 0 to 4.

17. A process for producing naphthalocyanine derivative which comprises the step of: reacting amino metallo or non-metallo naphthalocyanine selected from the group consisting of tetraamino metallo or non-metallo naphthalocyanines, and octaamino metallo or non-metallo naphthalocyanines, with o-sulfobenzoic acid anhydride in the presence of a reaction accelerator in an aprotic organic solvent.

18. Aqueous ink for ink-jet printing which comprises water, and the naphthalocyanine derivative according to claim 11 as a colorant.

19. Color filter which comprises the phthalocyanine derivative according to claim 11 as a colorant.

20. Photorecording materials which comprise the phthalocyanine derivative according to claim 11 as a colorant.

* * * * *